United States Patent [19]

Chu et al.

[11] Patent Number: 4,605,787
[45] Date of Patent: Aug. 12, 1986

[54] PROCESS FOR THE PREPARATION OF ALKYL TERT-ALKYL ETHERS

[75] Inventors: Pochen Chu, West Deptford; Guenter H. Kuehl, Cherry Hill, both of N.J.

[73] Assignee: Mobil Oil Corporation, New York, N.Y.

[21] Appl. No.: 742,375

[22] Filed: Jun. 10, 1985

Related U.S. Application Data

[63] Continuation of Ser. No. 641,412, Aug. 16, 1984, abandoned, which is a continuation of Ser. No. 532,939, Sep. 16, 1983, abandoned, which is a continuation of Ser. No. 232,800, Feb. 9, 1981, abandoned, which is a continuation of Ser. No. 121,759, Feb. 15, 1980, abandoned.

[51] Int. Cl.$^4$ ............................................. C07C 41/05
[52] U.S. Cl. ..................................... 568/697; 568/698
[58] Field of Search ............................... 568/687, 699

[56] References Cited

U.S. PATENT DOCUMENTS 3,170,000  2/1965  Verdol .
3,726,942  4/1973  Louder .
3,728,408  4/1973  Tobias .
3,966,586  1/1976  Owen et al. .

FOREIGN PATENT DOCUMENTS 133661    1/1979   Fed. Rep. of Germany .
103379    8/1979   Poland .
1369889  10/1974   United Kingdom .

OTHER PUBLICATIONS

Hersh, Molecular Sieves, Reinhold Publishing, New York, pp. 29-30, 44-45, 78-79.
Venuto, Chem. Tech., Apr. 1, 1971, pp. 215-224.

*Primary Examiner*—Howard T. Mars
*Attorney, Agent, or Firm*—A. J. McKillop; M. G. Gilman; L. G. Wise

[57] ABSTRACT

Process for the preparation of alkyl tert-alkyl ethers which comprises reacting a primary alcohol with an olefin having a double bond on a tertiary carbon atom in the presence of an acidic zeolite catalyst. Removal of any excess alcohol from the reaction product is accomplished by passing the reaction product through a bed of small pore zeolite.

5 Claims, 2 Drawing Figures

PROCESS FOR THE PREPARATION OF ALKYL TERT-ALKYL ETHERS

This application is a continuation of application Ser. No. 641,412, filed Aug. 16, 1984, now abandoned, which is a continuation of application Ser. No. 532,939, filed Sept. 16, 1983, now abandoned, which is a continuation of application Ser. No. 232,800, filed Feb. 9, 1981, now abandoned, which is a continuation of application Ser. No. 121,759, filed Feb. 15, 1980, now abandoned.

BACKGROUND OF THE INVENTION

1. Field of the Invention

This invention relates to a process for producing alkyl tert-alkyl ethers useful, among other things, as octane improvers in gasoline compositions.

2. Description of the Prior Art

It is known that alkyl tert-alkyl ethers can be prepared by reacting a primary alcohol with an olefin having a double bond on a tertiary carbon atom, thus methanol reacts with isobutylene and isopentenes (2 methyl 1-butene or 2 methyl 2-butene) to form respectively methyl tert-butyl ether (MTBE) and methyl tert-amyl ether (MTAE).

The reaction is selective for tertiary olefins so that it constitutes a valid process for their removal from olefinic streams in which they are contained together with linear unreactive olefins.

The reaction has an equilibrium which is the more favorable to the synthesis of the ether the lower the reaction temperature in accordance with its negative enthalpy.

It is known that the reaction is catalyzed by Lewis acids (aluminium trichloride, boron trifluoride), mineral acids (sulphuric acid) and organic acids (alkyl and aryl sulphonic acids, ion exchange resins).

Particularly suitable for the task are ion exchange resins in their acid form and it is known that the best results are obtained by means of macroreticular resins of the type "Amberlyst 15".

By means of such last named catalysts it is possible to reach thermodynamic equilibrium within industrially acceptable contact times in the temperature range of 50°–60° C.

At lower temperatures, thermodynamically more favorable, the kinetics are not sufficiently favorable to permit reaching equilibrium in practice.

This fact limits conversions.

Obviously the conversion of a reagent can be increased by increasing in the feed the content of the other reagent but this involves a lowering of the conversion of the excess reagent.

This can cause some drawbacks, as for instance in the synthesis of MTBE starting from methanol and isobutylene contained in an olefinic stream, the use of excess isobutylene involves the fact that the olefinic stream after separation of MTBE still contains 5–10% isobutylene and this constitutes a drawback when such stream has to be utilized for the production of maleic anhydride or butadiene. On the other hand an excess of methanol renders the purification of MTBE very expensive because of the formation of azeotropes.

It is to overcome the foregoing drawbacks in the production of tert-alkyl ethers that this invention is directed by employing a zeolitic catalyst material instead of an ion-exchange resin. Not only are the zeolitic catalysts substantially perfectly stable (which ion-exchange resins are not) but they also suppress formation of diisobutylene during the conversion to tert-alkyl ethers.

Unable to meet the demand for unleaded gasoline, petroleum refiners are turning to other chemicals to extend available supplies and obtain more usable fuel out of a barrel of oil. The chemicals, compounds of carbon, hydrogen and oxygen, contain no metal and avoid the environmental problems associated with tetraethyl lead and MMT (methylcyclopentadienyl manganese tricarbonyl).

Currently much of the interest in these blending agents centers on methyl tert-butyl ether, MTBE, which has been approved for use in motor fuels in concentrations of up to 7 percent by the Environmental Protection Agency.

Since MTBE is derived from crude oil fractions unsuitable by themselves for use in gasoline, simply adding it to the mixture called gasoline adds to gasoline supplies; but MTBE has another useful property; it enhances the octane rating of gasoline.

SUMMARY OF THE INVENTION

In accord with the invention there has now been found a process for the preparation of alkyl tert-alkyl ethers by a method which comprises reacting primary alcohols with an olefin having a double bond on a tertiary carbon atom in the presence of an acidic zeolite catalyst characterized by having a constraint index of from about 1 to 12, and a silica/alumina ratio of at least about 5. Removal of any excess alcohol from the reaction product is accomplished by adsorption on a small pore zeolite.

DESCRIPTION OF PREFERRED EMBODIMENTS

Figure 1:
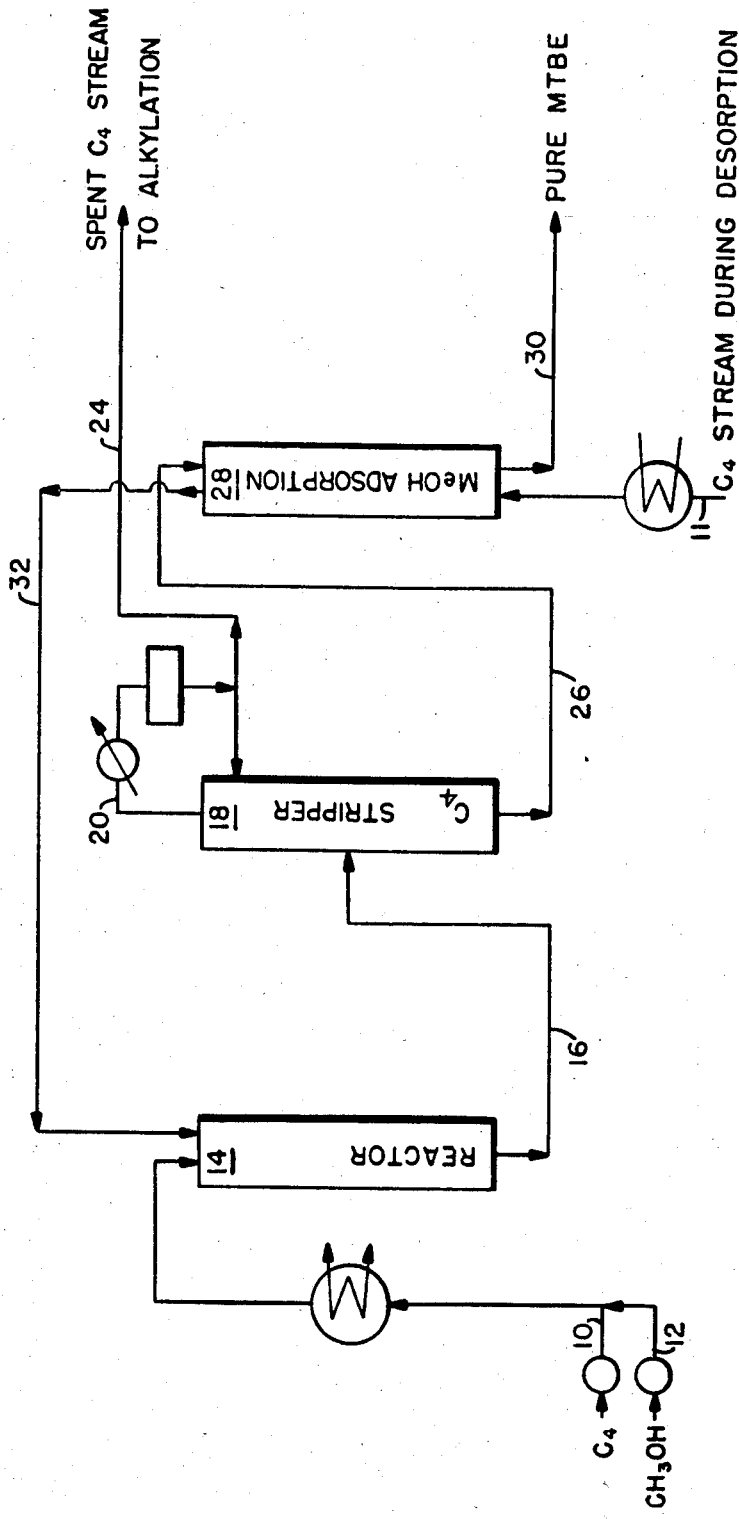
FIG. 1 is a block-flow diagram illustrating how the invention process fits into a refinery set up.

The zeolite catalysts useful in this invention are characterized by a constraint index of from about 1 to 12, and preferably a $SiO_2/Al_2O_3$ mole ratio of at least about 5, non-limiting examples of which include zeolites ZSM-5, 11, 12, 23, dealuminized zeolite Y, and REALY. RE=Rare Earth.

Zeolite ZSM-5 is taught by U.S. Pat. No. 3,702,886. In a preferred synthesized form, the zeolite ZSM-5 for use in the catalyst composition useful in this invention has a formula, in terms of mole ratios of oxides in anhydrous state, as follows:

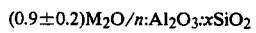

$(0.9\pm0.2)M_2O/n:Al_2O_3:xSiO_2$ wherein M is selected from the group consisting of a mixture of alkali metal cations, especially sodium, and tetraalkylammonium cations, the alkyl groups of which preferably contain 1 to 5 carbon atoms, and x is at least 5.

Zeolite ZSM-11 is taught by U.S. Pat. No. 3,709,979. In the as synthesized form, the zeolite ZSM-11 for use in the catalyst composition useful in this invention has a formula, in terms of mole ratios of oxides in the anhydrous state, as follows:

$(0.9\pm0.3)M_2O/n:Al_2O_3:zSiO_2$ wherein M is a mixture of at least one of the quaternary cations of a Group V-A element of the Periodic Table and alkali metal cations, especially sodium and z is at least 10.

Zeolite ZSM-12 is taught by U.S. Pat. No. 3,832,449. In the as synthesized form, the zeolite ZSM-12 for use in the catalyst composition useful in this invention has a formula, in terms of mole ratios of oxides in the anhydrous state, as follows:

$$(0.9\pm0.3)M_2O:n:Al_2O_3\cdot wSiO_2$$

wherein M is a mixture of at least one quaternary ammonium cation having the valence n, and alkali metal cations, especially sodium, and w is at least 20.

Zeolite ZSM-23 is described in U.S. Pat. No. 4,076,842.

In the as synthesized form, zeolite ZSM-23 for use in the catalyst composition useful in this invention, has a formula, in terms of mole ratios of oxides and in the anhydrous state, as follows:

$$(0.5-3.0)R_2O:(0.08-0.4)M_2O:Al_2O_3:(40-250)SiO_2$$

wherein R is a nitrogen-containing organic cation and M is an alkali metal cation.

Dealuminized zeolite Y may be prepared by a method described in U.S. Pat. No. 3,442,795 in which the $SiO_2/Al_2O_3$ ratio of crystalline aluminosilicates is increased by treating such aluminosilicates to remove part of the aluminum atoms in their anionic structure. Such removal is effected by a combined solvolysis-chelation technique, using ethylenediaminetetraacetic acid (EDTA).

An important characteristic of the crystal structure of the zeolites for use herein is that they provide constrained access to, and egress from, the intracrystalline free space by virtue of having a pore dimension greater than about 5 Angstroms and pore windows of about a size such as wound be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 5; and a structure providing constrained access to the intracrystalline free space.

The type zeolites useful in this invention freely sorb normal hexane and have a pore dimension greater than about 5 Angstroms. In addition, the structure must provide constrained access to large molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. But structures can be conceived due to pore blockage e.g. by cations, or other cause, they may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constrained index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts, including those useful herein, are

| Crystalline Aluminosilicate | CI |
|---|---|
| ZSM-5 | 8.3 |
| ZSM-11 | 8.7 |
| Clinoptilolite | 3.4 |
| ZSM-12 | 2 |
| ZSM-23 | 9.1 |
| ZSM-35 | 2 |
| ZSM-38 | 2 |
| Beta | 0.6 |
| ZSM-4 | 0.5 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, over variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

Members of the above group of zeolites for use in the catalyst composition of the present invention possess definite distinguishing crystalline structures as evidenced by the above U.S. Patents incorporated herein by reference.

In one preferred embodiment, methanol is reacted with isobutylene (i-$C_4H_8$) over an acid catalyst falling within the definition of the invention, such as HZSM-5, HZSM-12, and dealuminized zeolite Y at atmospheric pressure and a temperature range of between about 150° and 350° F., to produce methyl tert-butyl ether. It is known that the conversion of isobutylene increases with decreasing temperatures. It has been found that optimum temperature for most zeolites at atmospheric pressure is at about 180° F. As will be seen hereinbelow conversion of isobutylene is expected to increase significantly when carried out in liquid phase under a pressure required to keep the feed mixture liquid, e.g. of about 150–300 psig.

As described above, in a process for the production of methyl tertiary butyl ether (MTBE) or methyl tertiary amyl ether (MTAE), methanol is reacted with isobutylene or isopentene, respectively. In the prior art, a slight excess of methanol is required to suppress oligomerization of the olefin. The liquid product of the reaction is a mixture of MTBE (MTAE) with unreacted methanol and isobutene (isopentene) and inert $C_4$'s. Whereas the isobutene (isopentene) can be distilled off, the methanol forms an azeotrope with MTBE containing about 14 wt % (38.5 mol %) methanol. Therefore, with a molar ratio of $CH_3OH/i$-$C_4H_8$ in the charge of 1.2, half of the MTBE has to be recycled. The amount of MTBE to be recycled can be cut in half by applying pressure in the rectification.

Rather than performing a complicated rectification involving an azeotrope, it has been found in accord with another embodiment of the invention that the methanol can be removed from the reaction product by adsorption on a small-pore zeolite, e.g., zeolites 3A, 4A, 5A, or chabazite, and preferably 4A. Only methanol, which can be desorbed at higher temperature or lower pressure or a combination of both, is recycled. Instead of desorbing at reduced pressure, desorbing of the methanol in the $C_4$ feed stream is conducted at elevated temperature with the hydrocarbon feed as a purge. Thus the preheating of the reactor feed is combined with the desorption cycle of the adsorbers.

If MTBE is to be used as a gasoline octane booster, some oligomerization product, mainly diisobutene, as found in the prior art, can be tolerated. In such a case a smaller or no excess of methanol can be applied resulting in a product that consists mainly of MTBE and small amounts of isobutene, diisobutene and methanol. Again, if desired, the methanol can be removed from the mixture by adsorption on a small-pore zeolite. The same desorption schemes can be applied.

If highly pure MTBE is to be obtained, in the prior art, either an excess of methanol, e.g., 1.2:1, is applied in the catalytic reaction thus causing a large amount of MTBE to be recycled in the rectification. If adsorbers are employed, a higher load on the adsorbers is caused by the large excess of methanol. Oligomerized impurities, mainly diisobutene, can be removed only by distilling the MTBE.

With reference to the accompanying FIG. 1, the process which is the subject of the present invention will now be illustrated for the particular case of the preparation of MTBE, even though as noted above, the process is valid for the preparation of other alkyl tertiary alkyl ethers, the drawing being intended as not restrictive of the invention itself.

A $C_4$ fraction 10 is mixed with methanol 12, preheated and introduced into the reactor 14. The effluent 16 flows to a stripper 18 in which the unreacted $C_4$ hydrocarbons 20 are removed and led 24 to the alkylation unit. Methanol is removed from the bottom fraction 26 by adsorption on, e.g., 4A zeolite in a dual column adsorption-desorption unit 28. The effluent 30 from the adsorber 28 is essentially pure MTBE, containing <0.5% of TBA and no methanol; it can be blended directly with gasoline to obtain a higher octane rating. The adsorbed methanol is desorbed with a combination of heat and reduced pressure. The heat can be supplied with a preheated $C_4$ feed stream 11. The desorbed methanol, together with the $C_4$ feed, is recycled 32 to the reactor 14.

Figure 2:
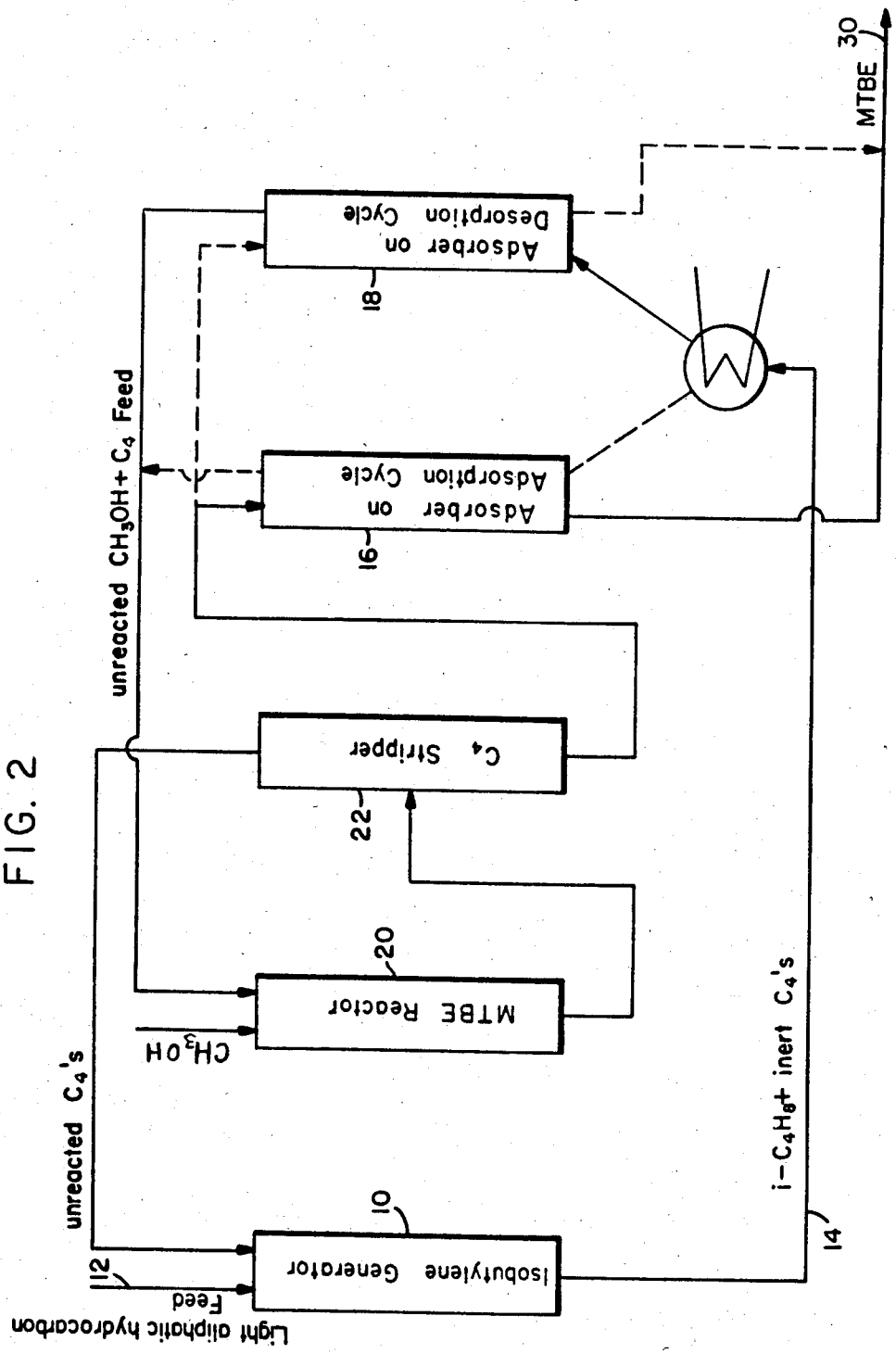
FIG. 2 is a block-flow diagram illustrating a self-contained MTBE plant.

FIG. 2 is a block-flow diagram showing a self-contained MTBE plant. Isobutylene is produced in an isobutylene generator 10, which is not part of this invention, by charging a light hydrocarbon feed 12. A $C_4$-stream 14 from this unit, after removal of by-products, contains isobutylene and inert $C_4$ hydrocarbons. This stream is heated and passed through an adsorption column 18 containing zeolite 4A loaded with methanol. The methanol is desorbed 18 and the mixed methanol-$C_4$ stream is charged, together with fresh methanol feed, to the MTBE reactor 20. Unreacted $C_4$'s are removed from the MTBE product in a $C_4$ stripper 22 and returned to the isobutylene generator. The stripper bottoms consist of MTBE with some unreacted methanol. This stream is passed to an adsorber 16 filled with, e.g. zeolite 4A which removes the methanol by adsorption. The effluent of the adsorber is pure MTBE 30. The adsorbed methanol is then again desorbed in the desorption cycle with the preheated $C_4$ stream, as described above.

The invention will be further described in conjunction with the following non-limitative examples.

Examples 1 (a–b), 2 (a–d), 3 (a–c), 4, 5 (a–b), 6 (a–c), 7 (a–d), 8 (a–b) and 9 (a–c) compiled in tabular form as Table I shows the manufacture of methyl tert-butyl ether over various zeolite catalysts in the vapor phase.

TABLE 1

| | | | | | | | | | | | | | |
|---|---|---|---|---|---|---|---|---|---|---|---|---|---|
| Formation of MTBE Over Zeolite Catalyst | | | | | | | | | | | | | |
| | Example 1 | | Example 2 | | | | Example 3 | | | Example 4 | | Example 5 | |
| | (a) | (b) | (a) | (b) | (c) | (d) | (a) | (b) | (c) | (a) | (b) | (a) | (b) |
| Catalyst | | | | | | | | | | | | | |
| Zeolite Type | H-Mordenite | | H-Beta | → | → | → | REHY | → | → | REA1Y | → | HZSM-35 | → |
| $SiO_2/Al_2O_3$ | 26 | → | 22 | → | → | → | 5.3 | → | → | 5.1 | → | 23 | → |
| Wt of Zeolite, g | 1.0 | → | → | → | → | → | → | → | → | → | → | 0.65 | → |
| Wt of $Al_2O_3$ Binder, g | 0 | → | → | → | → | → | → | → | → | → | → | 0.35 | → |

TABLE 1-continued

Formation of MTBE Over Zeolite Catalyst

| Charge | | | | | | | | | | | | | | |
|---|---|---|---|---|---|---|---|---|---|---|---|---|---|---|
| Methanol, cc/hour | 1.6 | → | → | → | → | → | → | → | → | → | → | → | → | → |
| Isobutene, cc/min | 15 | → | → | → | → | → | → | → | → | → | → | → | → | → |
| Molar Ratio, CH$_3$OH/i-C$_4$= | 1.0 | → | → | → | → | → | → | → | → | → | → | → | → | → |
| WHSV, total charge[1] | 3.44 | → | → | → | → | → | → | → | → | → | → | → | 5.29 | → |
| Pressure, PSIG | 0 | → | → | → | → | → | → | → | → | → | → | → | → | → |
| Temperature, set, °F. | 150 | 180 | 200 | 150 | 180 | 200 | 150 | 180 | 200 | 180 | 200 | 180 | 200 |
| Temperature, peak, °F. | 168 | 192 | 212 | 165 | 196 | 216 | 155 | 193 | 210 | 181 | 209 | 181 | 202 |
| Product Analysis CH$_3$OH/i-C$_4$H$_8$ of charge | 1.25 | 1.07 | 1.14 | 1.25 | 1.46 | 1.53 | 1.16 | 1.20 | 1.18 | 1.06 | 1.04 | 1.15 | 1.23 |
| Conversion of i-C$_4$H$_8$ | | | | | | | | | | | | | | |
| to MTBE, % | 4.8 | 8.4 | 7.1 | 20.8 | 13.9 | 9.1 | 0.8 | 11.3 | 10.6 | 25.3 | 23.4 | 0.13 | 0.41 |
| to C$_8$ Olefin, % | 1.15 | 6.0 | 14.1 | 13.2 | 23.0 | 27.3 | 0 | 0.47 | 1.88 | 0.3 | 1.25 | 0 | 0 |
| Selectivity to MTBE, % | 80.7 | 58.3 | 33.5 | 61.2 | 37.7 | 25.0 | 100 | 96.0 | 85.0 | 98.8 | 94.9 | 100 | 100 |

| | Example 6 | | | Example 7 | | | | Example 8 | | Example 9 | | |
|---|---|---|---|---|---|---|---|---|---|---|---|---|
| | (a) | (b) | (c) | (a) | (b) | (c) | (d) | (a) | (b) | (a) | (b) | (c) |
| Catalyst | | | | | | | | | | | | |
| Zeolite Type | HZSM-5 | → | → | HZSM-5 | → | → | → | HZSM-5 | → | HZSM-11 | → | → |
| SiO$_2$/Al$_2$O$_3$ | 70 | → | → | 70 | → | → | → | 40 | → | 20 | → | → |
| Wt of Zeolite, g | 1.0 | → | → | 0.65 | → | → | → | → | → | 1.0 | → | → |
| Wt of Al$_2$O$_3$ Binder, g | 0 | → | → | 0.35 | → | → | → | → | → | 0 | → | → |
| Charge | | | | | | | | | | | | |
| Methanol, cc/hour | 1.6 | → | → | → | → | → | → | → | → | → | → | → |
| Isobutene, cc/min | 15 | → | → | → | → | → | → | → | → | → | → | → |
| Molar Ratio, CH$_3$OH/i-C$_4$= | 1.0 | → | → | → | → | → | → | → | → | → | → | → |
| WHSV, total charge[1] | 3.44 | → | → | 5.29 | → | → | → | → | → | 3.44 | → | → |
| Pressure, PSIG | 0 | → | → | → | → | → | → | → | → | → | → | → |
| Temperature, set, °F. | 180 | 200 | 220 | 170 | 180 | 200 | 220 | 180 | 200 | 170 | 180 | 200 |
| Temperature, peak, °F. | 195 | 209 | 226 | 185 | 197 | 211 | 228 | 196 | 211 | 188 | 200 | 212 |
| Product Analysis CH$_3$OH/i-C$_4$H$_8$ of charge | 1.06 | 1.05 | 1.09 | 1.10 | 1.20 | 1.12 | 1.06 | 1.08 | 0.98 | 1.05 | 0.98 | 0.98 |
| Conversion of i-C$_4$H$_8$ | | | | | | | | | | | | |
| to MTBE, % | 30.5 | 25.3 | 18.6 | 23.6 | 27.6 | 25.9 | 18.7 | 26.2 | 21.8 | 24.6 | 25.1 | 21.0 |
| to C$_8$ Olefin, % | 0 | 0.1 | 0.15 | 0 | 0 | 0 | 0 | 0 | 0 | 0 | 0.14 | 0.21 |
| Selectivity to MTBE, % | 100 | 99.6 | 99.2 | 100 | 100 | 100 | 100 | 100 | 100 | 100 | 99.4 | 99.0 |

[1]per g of zeolite

The conversion of i-C$_4$H$_8$ increased with decreasing temperature; however, HZSM-12 gave no conversion at 150° F. It appears that the optimum temperature for most zeolites at atmospheric pressure, is in the vicinity of 180° F. The selectivity to MTBE increases also with decreasing temperature, ie., the olefin oligomerization reaction is reduced at lower temperature.

The following examples compiled in tabular form illustrated the conversion of i-C$_4$H$_8$ in liquid phase under pressure of 150-200 psig in the presence of HZSM-5 and HZSM-11, respectively.

TABLE 2

Reaction of i-C$_4$H$_8$ with CH$_3$OH over HZSM-5 Extrudate

| | Temperature | | | | Conversion of | Conversion of |
|---|---|---|---|---|---|---|
| Example | Peak °F. | Reactor Bottom °F. | WHSV[1] | CH$_3$OH i-C$_4$H$_8$ | i-C$_4$H$_8$ % | CH$_3$OH, % |
| 6 | 221 | 175 | 1.85 | 0.88 | | 91.6 |
| 7 | 222 | 174 | 1.82 | 0.92 | | 90.6 |
| 8 | 226 | 173 | 1.75 | 0.97 | | 89.6 |
| 9 | 228 | 174 | 1.46 | 1.31 | 93.0 | |
| 10 | 230 | 174 | 1.40 | 1.43 | 94.2 | |
| 11 | 229 | 174 | 1.38 | 1.50 | 94.3 | |
| 12 | 228 | 184 | 1.62 | 1.21 | 91.3 | |
| 13 | 227 | 163 | 1.51 | 1.36 | 93.1 | |
| 14 | 249 | 184 | 1.28 | 1.17 | 89.0 | |

[1]Based on zeolite

The catalyst used for the Examples listed in Table 2 was hydrogen ZSM-5, having a SiO$_2$/Al$_2$O$_3$ molar ratio of 40. The results show 90-94% conversion of the stoichiometrically minor component in the feed mixture. Formation of diisobutylene by oligomerization of isobutylene was not observed except for a very minor amount in Example 6, having the highest excess of isobutylene; less than 0.05% of isobutylene was converted to diisobutylene in this run. The suppression of the oligomerization side reaction is one of the advantages of this catalyst. As Example 14 indicates, higher reaction temperature was deleterious to the conversion, as the equilibrium

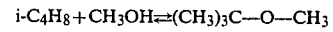

$$i\text{-}C_4H_8 + CH_3OH \rightleftharpoons (CH_3)_3C\text{-}O\text{-}CH_3$$

shifts to the left with increasing temperature. The catalyst showed no loss in activity or selectivity in seven days.

TABLE 3

Reaction of i-C$_4$H$_8$ with CH$_3$OH over HZSM-11

| | Temperature | | | | Conversion of |
|---|---|---|---|---|---|
| Example | Peak °F. | Bottom Reactor °F. | WHSV | CH$_3$OH i-C$_4$H$_8$ | i-C$_4$H$_8$, % |
| 15 | 186 | 173 | 1.41 | 1.05 | 88.7 |
| 16 | 199 | 174 | 1.39 | 1.13 | 90.9 |
| 17 | 192 | 163 | 1.36 | 1.16 | 91.4 |
| 18 | 199 | 167 | 1.06 | 1.66 | 95.6 |

Another zeolite useful as catalyst in this reaction is hydrogen ZSM-11. The material used had a SiO$_2$/Al$_2$O$_3$ molar ratio of 25. The results listed in Table 3 showed the same conversion levels as with ZSM-5 with this more active catalyst at a lower temperature.

The percentage of i-C$_4$H$_8$ converted to tert.butyl alcohol can be reduced considerably by passing the methanol feed stream through a drying column containing 3A zeolite. In this manner we have been able to reduce the conversion of i-$C_4H_8$ to TBA from about 1.0% to about 0.25%.

The following example illustrated the removal of methanol from a mixture containing the same with tert-butyl alcohol and MTBE.

EXAMPLE 19

Dehydrated zeolite 4A extrudate, 10.0 g. was placed in a column, and a liquid mixture containing 8.2 wt % of methanol, 5.3 wt % tert.butyl alcohol and 86.5 wt % MTBE was passed through the bed. The effluent was divided into three fractions. None of these fractions contained any methanol, whereas tert.butyl alcohol and MTBE were not sorbed.

The following examples illustrated adsorption vs. desorption at increasing temperatures.

EXAMPLE 20

Zeolite 4A containing 12.5 g of adsorbed methanol per 100 g. of zeolite, was calcined in an inert gas stream at a heating rate of 20° C. min. The fastest desorption rate was achieved at about 175° C., and all methanol was desorbed at 250° C.

EXAMPLE 21

Zeolite 4A containing adsorbed methanol was calcined in an inert gas stream at 175° C. All methanol was removed at this temperature. Analysis of the gas stream showed methanol being desorbed without forming by-products.

What is claimed is:

1. A process for the preparation of methyl tert-butyl ether which comprises reacting in vapor phase at a temperature between 170°–220° F. methanol with isobutylene in the presence of a ZSM-5 or ZSM-11 acidic zeolite catalyst characterized by having a constraint index of from about 1 to 12 and a silica/alumina ratio of at least about 5.

2. A process for the preparation of methyl tert-butyl ether which comprises reacting in vapor phase at a temperature between 170°–220° F. methanol with isobutylene in the presence of a ZSM-5 or ZSM-11 acidic zeolite catalyst, said methanol being present in excess of that needed for reaction purposes, to form the reaction product methyl tert-butyl ether in admixture with unreacted methanol and contacting the admixture with a zeolite acting as a sorbent and capable of selectively sorbing said methanol and recovering the substantially methanol-free reaction product.

3. The process of claim 2 wherein said zeolite acting as a sorbent is zeolite 3A, 4A, 5A or chabazite.

4. A process for the preparation of methyl-tert-butyl ether which comprises reacting methanol with isobutylene under a pressure sufficient to maintain liquid phase conditions in the presence of a ZSM-5 or ZSM-11 acidic zeolite catalyst characterized by having a constraint index of from about 1 to 12 and a silica/alumina ratio of at least about 5, and thereafter recovering methyl-tert-butyl ether.

5. A process in accordance with claim 4 wherein the reaction is conducted at a pressure of about 150–300 psig.

* * * * *